United States Patent
Kim

(10) Patent No.: US 7,727,494 B2
(45) Date of Patent: Jun. 1, 2010

(54) CHILD CARE STORAGE HAVING STEAM STERILIZING APPARATUS

(75) Inventor: Young Jae Kim, Seoul (KR)

(73) Assignee: Daewoo Electronics Corporation, Seoul (KR)

( * ) Notice: Subject to any disclaimer, the term of this patent is extended or adjusted under 35 U.S.C. 154(b) by 1131 days.

(21) Appl. No.: 11/362,078

(22) Filed: Feb. 27, 2006

(65) Prior Publication Data

US 2006/0222579 A1    Oct. 5, 2006

(30) Foreign Application Priority Data

Mar. 29, 2005   (KR) .................. 10-2005-0025777

(51) Int. Cl.
| | |
|---|---|
| A61L 2/08 | (2006.01) |
| A61L 2/00 | (2006.01) |
| H05B 1/00 | (2006.01) |
| F27D 11/00 | (2006.01) |
| B08B 3/00 | (2006.01) |
| F22B 1/30 | (2006.01) |
| F22B 5/00 | (2006.01) |
| H01B 17/00 | (2006.01) |

(52) U.S. Cl. .......................... 422/307; 422/1; 422/26; 422/295; 422/297; 422/298; 422/299; 422/300; 422/305; 422/308; 219/200; 219/243; 219/385; 219/428; 219/431; 219/429; 219/432; 219/436; 219/647; 134/148; 134/153; 134/108; 134/160; 134/169 R; 134/56 R; 134/105; 392/336; 392/338; 174/137 R; 122/13.01

(58) Field of Classification Search ............... 422/1, 422/26, 295, 297–300, 305, 307–308; 219/200, 219/243, 385, 428, 431, 429, 432, 436, 647; 134/148, 153, 108, 160, 169 R, 56 R, 105; 392/336, 338; 174/137 R; 122/13.01
See application file for complete search history.

(56) References Cited

U.S. PATENT DOCUMENTS

| | | | |
|---|---|---|---|
| 5,213,776 A | | 5/1993 | Maniero et al. |
| 5,507,060 A | * | 4/1996 | Quimpo .......................... 15/63 |
| 5,756,968 A | * | 5/1998 | Chung .......................... 219/428 |
| 6,809,302 B1 | * | 10/2004 | Jones et al. .................. 219/521 |
| 2003/0124024 A1 | | 7/2003 | Chang |

FOREIGN PATENT DOCUMENTS

| | | |
|---|---|---|
| DE | 8021633 | 11/1980 |
| EP | 183956 | 6/1986 |
| EP | 718000 | 6/1996 |
| GB | 2378901 | 2/2006 |

* cited by examiner

*Primary Examiner*—Jill Warden
*Assistant Examiner*—Monzer R Chorbaji
(74) *Attorney, Agent, or Firm*—Bacon & Thomas, PLLC

(57) ABSTRACT

A child care storage having a steam sterilizing apparatus, wherein the steam sterilizing apparatus includes an outer tub defined by walls of a steam sterilizing compartment; a hollow upstanding coupling member installed on the center bottom of the outer tub and having an interlocking hole formed at its top; an inner tub inserted inside the outer tub for accommodating infant accessories therein, the inner tub having a reception hole formed at its bottom center and a latch part formed along the circumference of its bottom center; an evaporation vessel having a flange along its circumference, the flange being coupled to the latch part of the inner tub; a flat-type heater installed under a rear bottom surface of the evaporation vessel; and a supporting plate for placing the flat-type heater thereon.

5 Claims, 4 Drawing Sheets

CHILD CARE STORAGE HAVING STEAM STERILIZING APPARATUS

FIELD OF THE INVENTION

The present invention relates to a child care storage having a steam sterilizing apparatus, and, more particularly, to a child care storage having a steam sterilizing apparatus capable of being easily attachable and detachable for cleaning and/or repair.

BACKGROUND OF THE INVENTION

Recently, with a rise in the standard of living, there have been increasing demands for diversified types of special-purpose refrigerators, for example, a kimchi refrigerator for the ripening of kimchi, a cosmetic cooler for storing cosmetics at a low temperature and so forth.

Though such various types of special-purpose refrigerators have been developed, developments have rarely been made upon a storage apparatus for an exclusive use in baby or child care.

If infant food or infant products such as powdered milk, breast milk, medicine and the like are stored in a conventional household refrigerator, they will be soaked with the odors of other foods stored in the refrigerator. As a result, the quality of the infant food or the infant products will be deteriorated and, even worse, hygienic problems may be resulted.

Therefore, there is a need to develop a multi-functional child care storage including a plurality of functional compartments for storing or treating infant food or infant products in various ways.

In order to meet the need, there has been suggested a multi-functional child care storage, for example, which is disclosed in a co-pending, commonly owned application, International Application No. PCT/KR2006/000575 filed on Feb. 21, 2006, entitled 'MULTI-FUNCTIONAL CHILD CARE STORAGE', which is hereby incorporated by reference. The multi-functional child care storage has a plurality of functional compartments. Among them, a steam sterilizing compartment accommodates infant products such as a baby bottle, a handkerchief, a gauze, a toy and so forth, and sterilizes these by hot steam.

FIG. 1 schematically shows the steam sterilizing compartment of the multi-functional child care storage. The steam sterilizing compartment 140 has a door 143 at its top by being closed and opened to define a sterilizing space 141, and a steam sterilizing unit 142 to disinfect the sterilizing space 141 by hot steam.

The steam sterilizing unit 142 is placed in the steam sterilizing compartment 140 such that it closely fits on the surface of walls 112. Moreover, the steam sterilizing unit 142 includes a rack holder 142d having a plurality of steam passage holes 142f thereon; an evaporation vessel 142a molded from stainless steel or the like, which is placed below the rack holder 142d and accommodates water therein; a heater 142b placed underneath the evaporation vessel 142a to uniformly heat the evaporation vessel 142a and vaporize water within the evaporation vessel 142a into the sterilizing space 141; a steam outlet 142c incorporated with the door 143 for discharging steam from the sterilizing space 141; a cover 142i mounted on the steam outlet 142c for preventing a user from injuries caused by releasing steam, and forcibly emitting hot steam toward the rear thereof; a rack 142e on which a plurality of upstanding supports 142g are mounted to receive the infant accessory thereon, further having steam passage holes 142j which are formed at its bottom.

Therefore, as described above, it is possible to sterilize the baby bottle 1 stored in the sterilizing space 141 by using hot steam generated by the steam sterilizing unit 142.

Meanwhile, in the steam sterilizing compartment 140, since the evaporation vessel 142a and the rack holder 142d become contaminated gradually in use, they are needed to be cleaned often.

However, there is a drawback that it is difficult to disassemble the evaporation vessel 142a from the steam sterilizing compartment 140.

Accordingly, it is preferable that the rack holder 142d and the evaporation vessel 142a are allowed to be easily released for cleaning and/or repair.

SUMMARY OF THE INVENTION

It is, therefore, an object of the present invention to provide a child care storage having a steam sterilizing apparatus capable of being attachable and detachable for ease cleaning and/or repair.

In accordance with a preferred embodiment of the present invention, there is provided a child care storage having a steam sterilizing apparatus, wherein the steam sterilizing apparatus including an outer tub defined by walls of a steam sterilizing compartment; a hollow upstanding coupling member installed on the center bottom of the outer tub and having an interlocking hole formed at its top; an inner tub inserted inside the outer tub for accommodating infant accessories and/or the like therein, the inner tub having a reception hole formed at its bottom center and a latch part formed along the circumference of its bottom center; an evaporation vessel having a flange along its circumference, wherein the flange is coupled to the latch part of the inner tub; a flat-type heater installed under a rear bottom surface of the evaporation vessel; and a supporting plate for placing the flat-type heater thereon.

BRIEF DESCRIPTION OF THE DRAWINGS

The above and other objects and features of the present invention will become apparent from the flowing description of preferred embodiments given in conjunction with the accompanying drawings, in which.

DETAILED DESCRIPTION OF THE INVENTION

Hereinafter, a preferred embodiment of the present invention will be described in detail with reference to the accompanying drawings.

Figure 1:
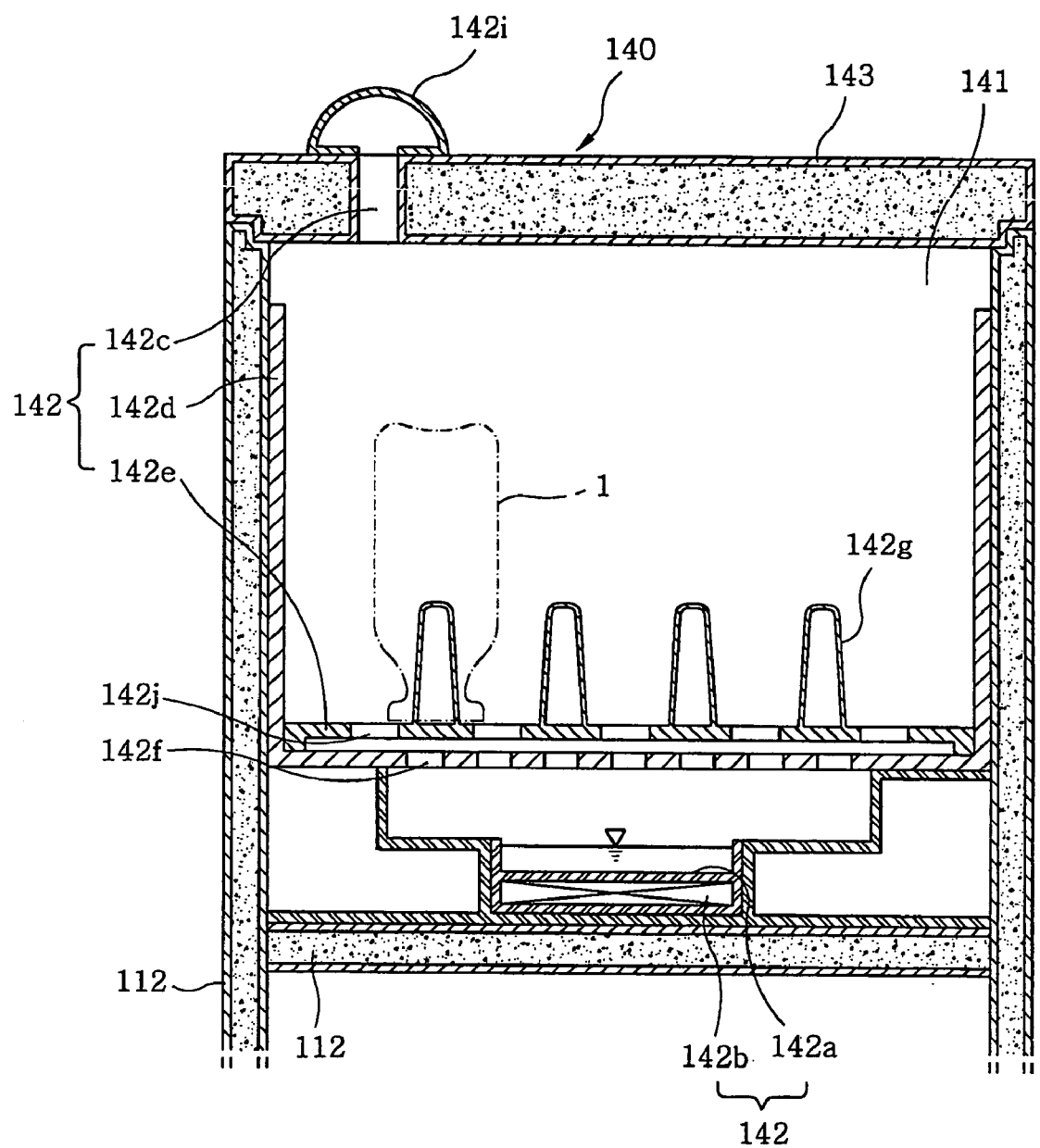
FIG. 1 is a sectional front elevation view of a steam sterilizing compartment incorporated in a conventional child care storage.
Figure 2:
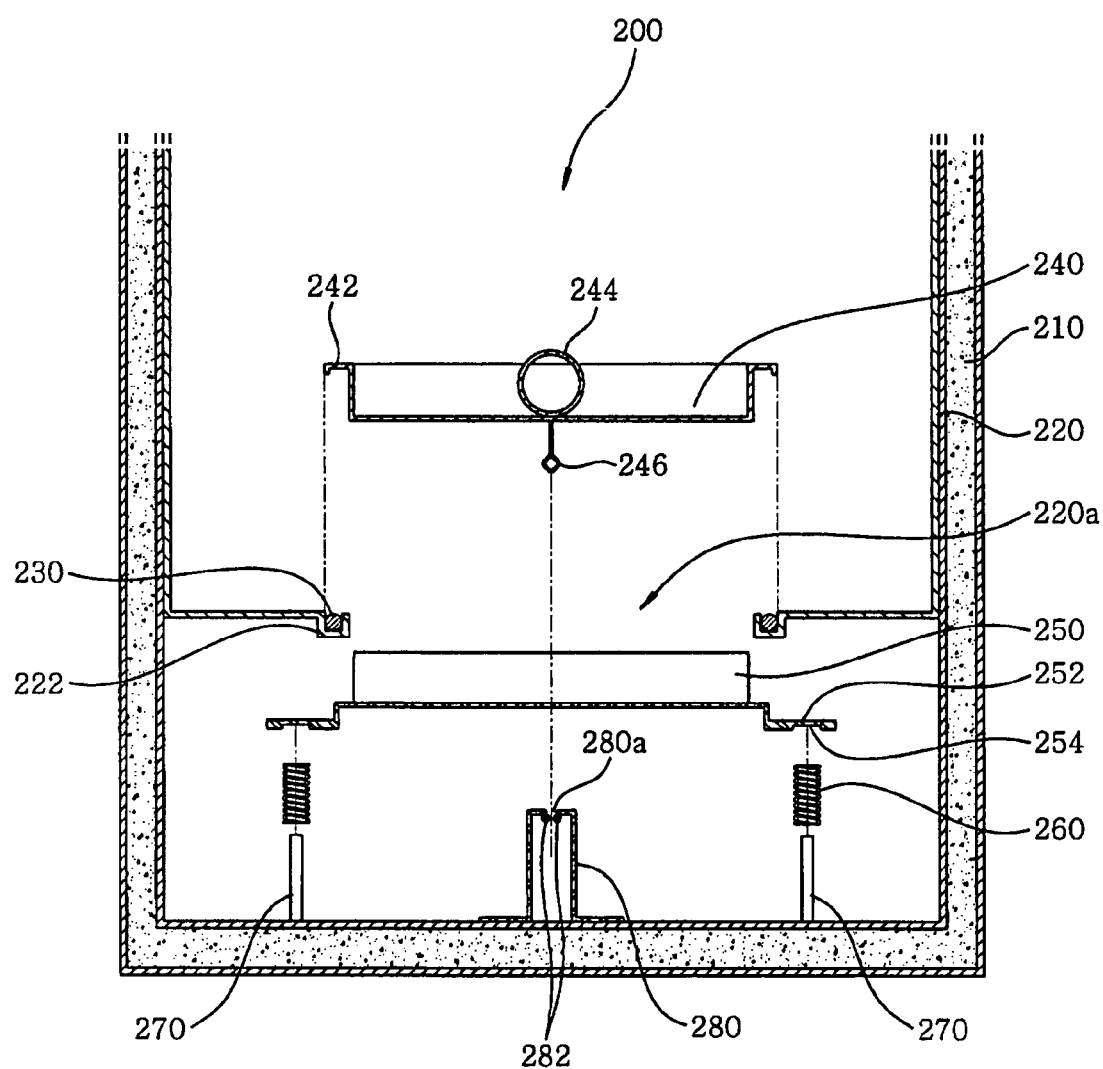
FIG. 2 is an exploded vertical sectional view of a steam sterilizing apparatus in accordance with the present invention.
Figure 3:
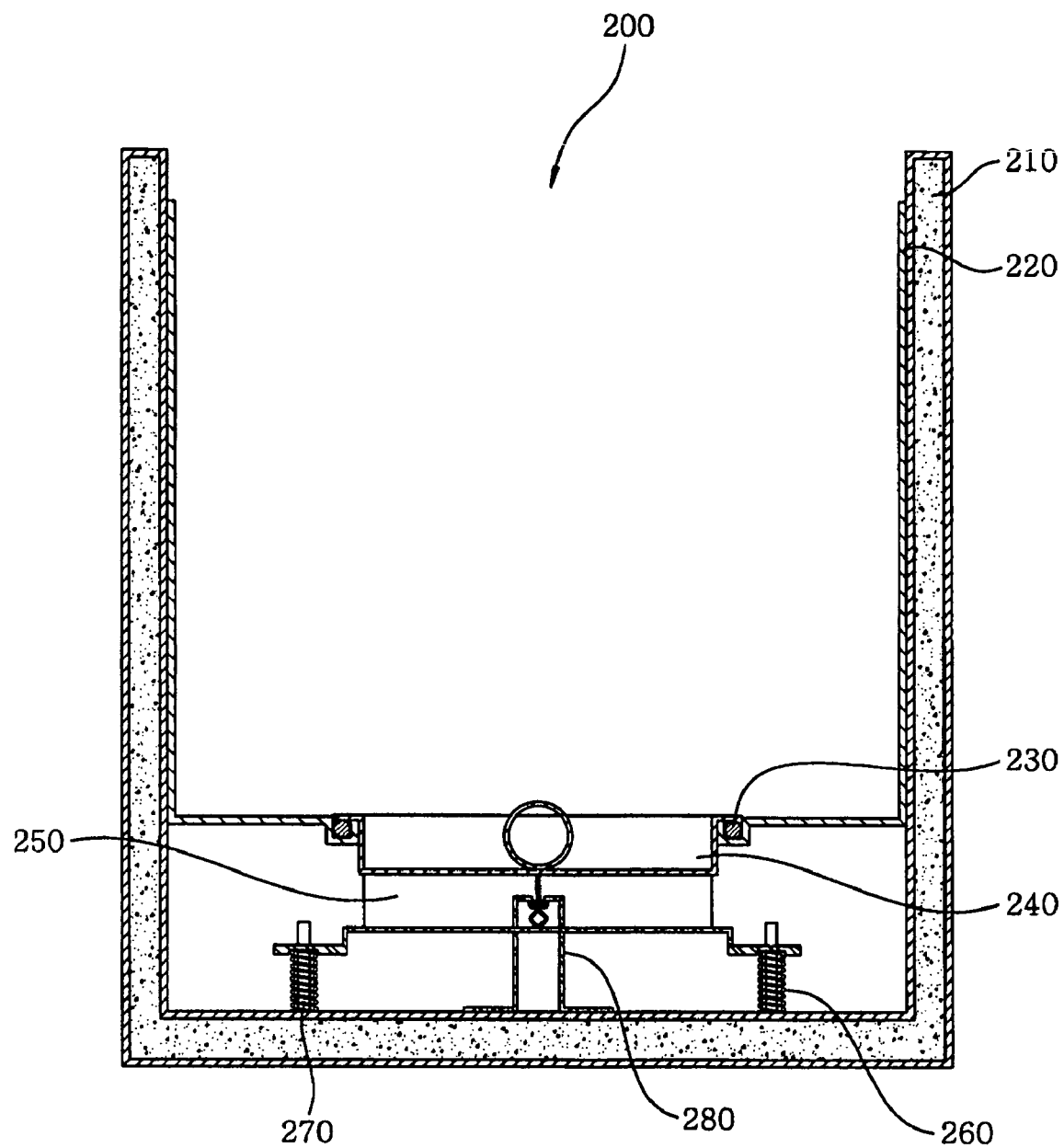
FIG. 3 shows an assembled vertical sectional view of a steam sterilizing apparatus in accordance with the present invention.

Referring now to FIGS. 2 and 3, there are shown an exploded vertical sectional view of a steam sterilizing apparatus; and an assembled vertical sectional view of a steam sterilizing apparatus.

As shown in these figures, the steam sterilizing apparatus 200 includes an outer tub 210 defined by walls of a steam sterilizing compartment, an inner tub 220 inserted into the outer tub 210, the inner tub 220 having a reception hole 220a formed at its bottom center, an evaporation vessel 240 containing water therein and coupled through the reception hole 220a at the bottom center of the inner tub 220, and a flat-type heater 250 located under the evaporation vessel 240 for heating uniformly the evaporation vessel 240 to generate hot steam.

The inner tub 220 is provided with a latch part 222 formed along its bottom center with the reception hole 220a, the latch part 222 extending downward and being upward. The evaporation vessel 240 is provided with a flange 242 formed along its outer circumference, the flange extending outward and being then bent downward, such that the flange 242 of the evaporation vessel 240 is coupled to the latch part 222 of the inner tub 220. Further, a packing element 230 such as a silicon packing element, is provided between the flange 242 of the evaporation vessel 240 and the latch part 222 of the inner tub 220, thereby, enabling to seal firmly between the latch 222 and the flange 242.

Also, a grip 244 is provided on the evaporation vessel 240 for the purpose of lifting upward the evaporation vessel 240 from the inner tub 220. And, an elastic projection 246 extends downwardly from the undersurface of the evaporation vessel 240.

In addition, a flat-type heater 250 is in contact with the undersurface of the evaporation vessel 240 and is supported on a supporting plate 252. The supporting plate 252 is provided with a stepped flange being outwardly extended. In addition, a concave portion 254 is formed at the lower surface of the flange of the supporting plate 252.

Further, an aperture or a through hole (not shown) is formed at the center of the flat-typed heater 250 and the supporting plate 252 so that the elastic projection 246 of the evaporation vessel 240 passes through the aperture or a through hole of the flat-type heater. Here, the flat-type heater 250 can be desirably U-shaped. Accordingly, the elastic projection 246 of the evaporation vessel 240 can also pass through the flat-type heater 250.

Further, a plurality of posts 270 are mounted on the inner bottom of the outer tub 210, on which the supporting plate 252 is mounted, and a hollow upstanding coupling member 280 is mounted on a bottom center of the outer tub 210. At a top of the hollow upstanding coupling member 280, and interlocking hole 280a is formed at a corresponding location to an elastic projection 246 so that the lower end of the elastic projection 246 is elastically fit into the interlocking hole 280a, thereby enabling elastic projection 246 to easily pass through the interlocking hole 280a and remove therefrom.

And, a plurality of resilient springs 260 are interposed in their corresponding upstanding supports 270 respectively, in order to provide a resilient force upwardly to the supporting plate 252.

Figure 4:
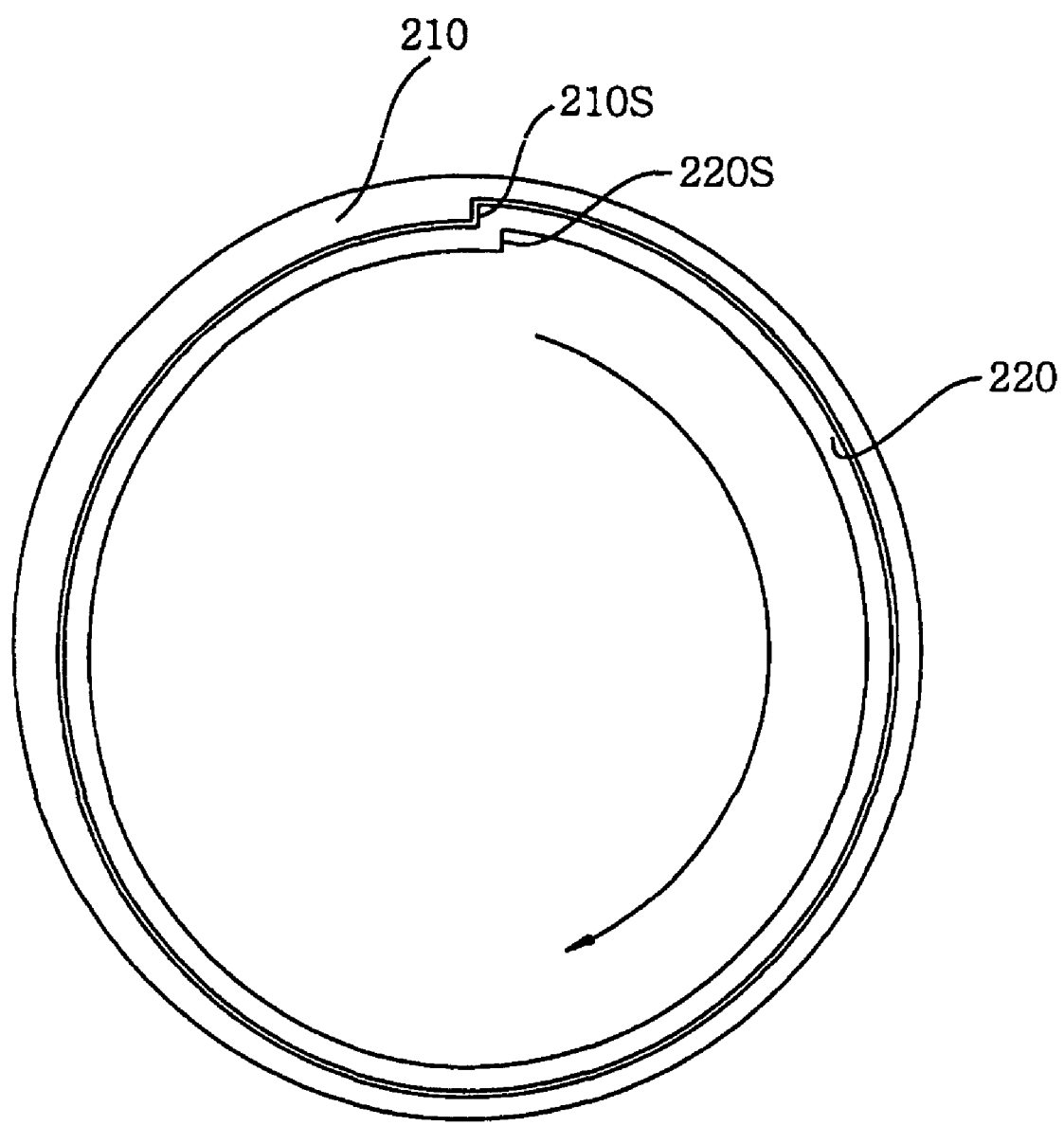
FIG. 4 is a cross sectional view of the assembly of the inner tub and the outer tub in accordance with the present invention.

Moreover, referring to FIG. 4, the inner tub 220 and the outer tub 210 have cylindrical shapes with stepped parts 220S and 210S in a longitudinal direction, respectively. Furthermore, the inner tub 220 and the outer tub 210 (particularly, the inner surface of the outer tub 210) are made flexible. Thus, when the inner tub 220 is inserted into the outer tub 210, by rotating the inner tub 220 to a predetermined direction, e.g., anti-clockwise direction as indicated by an arrow in FIG. 4, the inner tub 220 can be fit closely with the inner surface of the outer tub 210 by the associated help of the stepped parts 220S and 210S. The reason why the inner tub 220 should be firmly held by the outer tub 210 is to prevent the infant accessories from being fall down during a sterilizing operation, and to reduce noise and damage generated by the vibration.

Following is a description for assembling the steam sterilizing apparatus 200.

First of all, each resilient spring 260 is received by its corresponding upstanding support 270 and then, the flat-type heater 250 is mounted on the supporting plate 252 so that the concave portion 254 of the supporting plates 252 is resiliently held by the resilient spring 260.

Meanwhile, the evaporation vessel 240 is assembled by inserted into the inner tub 220 through the reception hole 220a. At this time, the flange 242 of the evaporation vessel 240 is coupled to latch part 222 of the inner tub 220, whereby they are firmly sealed by the packing element 230 therebetween.

After that, the inner tub 220 having the evaporation vessel 240 is fitted closely in the outer tub 210 at the predetermined position. At this time, as soon as the elastic projection 246 passes through the flat-type heater 250 and then elastically changes its shape within the interlocking hole 280a, the elastic projection 246 is coupled to the hollow upstanding coupling member 280 by means of small-sized rollers 282. Therefore, the bottom of the evaporation vessel 240 can become closely contact with the upper surface of the flat-type heater 250. Accordingly, resilient springs 260 are compressed downwardly a little and then, the inner tub 220 is firmly held by the outer tub 210 by means of rotating the inner tub 220 in a predetermined direction.

Since the evaporation vessel 240 is caught by the hollow upstanding coupling member 280 and further, the flat-type heater 250 is supported upwardly by a plurality of compressed resilient springs 260, the evaporation vessel 240 is attachably mounted on flat-type heater 250. Accordingly, it is possible to reliably seal between the evaporation vessel 240 and the flat-type heater 250, and to easily assemble the steam sterilizing apparatus 200.

Meanwhile, since the evaporation vessel 240 and the inner tub 220 become contaminated gradually in use, they are needed to be cleaned. To do it, first of all, by pulling the grip 244 of the evaporation vessel 240, the elastic projection 246 is released from the interlocking hole 280a due to its elastic deformation. Simultaneously, the flange 242 of the evaporation vessel 240 is uncoupled from the latch part 222 of the inner tub 220. As a result, the evaporation vessel 240 is separated from the flat-type heater 250.

Thereafter, in order to lift upward from the outer tub 210, the inner tub 220 is rotated to the outer tub 210 in a direction opposite to the direction of coupling. As a result, the flat-type heater 250 is exposed for cleaning or repairing. Accordingly, a user can conveniently wash the inner tub 220, the evaporation vessel 240 and the flat-type heater 250.

In addition, there is a pair of small-sized rollers 282 at a location where the interlocking hole 280a is formed in the hollow upstanding coupling member 280. The rollers 282 enable the elastic projection 246 to smoothly slide through the interlocking hole 280a.

While the invention has been shown and described with respect to the preferred embodiments, it will be understood by those skilled in the art that various changes and modifications may be made without departing from the spirit and scope of the invention as defined in the following claims.

What is claimed is:

1. A child care storage having a steam sterilizing apparatus, wherein the steam sterilizing apparatus comprises:

an outer tub defined by walls of a steam sterilizing compartment;

a hollow upstanding coupling member installed on the center bottom of the outer tub and having an interlocking hole formed at its top;

an inner tub inserted inside the outer tub for accommodating infant accessories therein, the inner tub having a reception hole formed at its bottom center and a latch part formed along the circumference of its bottom center;

an evaporation vessel having a flange along its circumference, wherein the flange is coupled to the latch part of the inner tub;

a flat-type heater installed under a rear bottom surface of the evaporation vessel;

a supporting plate for placing the flat-type heater thereon; and a plurality of springs interposed in their corresponding upstanding supports, respectively, in order to provide a resilient force upwardly to the supporting plate, whereby the bottom of the evaporation vessel becomes closely in contact with the upper surface of the flat-type heater, wherein the flat-type heater has a trough hole formed at the center thereof, and wherein the evaporation vessel has an elastic protection downwardly formed at rear surface of the evaporation vessel, the elastic projection passing through the through hole and then being inserted into the interlocking hole.

2. The child care storage as claimed in claim 1, wherein the inner tub includes a packing element the packing element being located between the flange and the latch part in order to closely seal with the evaporation vessel.

3. The child care storage as claimed in claim 1, wherein the evaporation vessel has a grip provided on an inner center bottom thereof, the grip upwardly allows the evaporation vessel to be disassembled from the inner tub.

4. The child care storage as claimed in claim 1, wherein the supporting plate has a plurality of concave portions formed at rear surface thereof on which the upstanding supports is arranged.

5. A child care storage having a steam sterilizing apparatus, wherein the steam sterilizing apparatus comprises:

an outer tub defined by walls of a steam sterilizing compartment;

a hollow upstanding coupling member installed on the center bottom of the outer tub and having an interlocking hole formed at its top;

an inner tub inserted inside the outer tub for accommodating infant accessories therein, the inner tub having a reception hole formed at its bottom center and a latch part formed along the circumference of its bottom center;

an evaporation vessel having a flange along its circumference, wherein the flange is coupled to the latch part of the inner tub;

a flat-type heater installed under a rear bottom surface of the evaporation vessel; and a supporting plate for placing the flat-type heater thereon, and wherein the hollow upstanding coupling member includes a number of rollers installed at a location where the interlocking hole is formed, the rollers enabling the elastic projection to smoothly slide through the interlocking hole.

* * * * *